(12) United States Patent
Novikov et al.

(10) Patent No.: US 10,853,948 B2
(45) Date of Patent: Dec. 1, 2020

(54) METHOD FOR AUTOMATICALLY DETECTING SYSTEMIC ARTERIES IN ARBITRARY FIELD-OF-VIEW COMPUTED TOMOGRAPHY ANGIOGRAPHY (CTA)

(71) Applicants: Agfa HealthCare GmbH, Vienna (AT); VRVIS ZENTRUM FÜR VIRTUAL REALITY UND VISUALISIERUNG, Vienna (AT)

(72) Inventors: Alexey Novikov, Mortsel (BE); David Major, Mortsel (BE); Maria Wimmer, Mortsel (BE); Katja Buehler, Mortsel (BE)

(73) Assignee: AGFA HEALTHCARE GMBH, Vienna (AT)

( * ) Notice: Subject to any disclaimer, the term of this patent is extended or adjusted under 35 U.S.C. 154(b) by 110 days.

(21) Appl. No.: 16/323,337

(22) PCT Filed: Aug. 9, 2017

(86) PCT No.: PCT/EP2017/070150
§ 371 (c)(1),
(2) Date: Feb. 5, 2019

(87) PCT Pub. No.: WO2018/029237
PCT Pub. Date: Feb. 15, 2018

(65) Prior Publication Data
US 2019/0172211 A1    Jun. 6, 2019

(30) Foreign Application Priority Data
Aug. 10, 2016    (EP) ...................................... 16183554

(51) Int. Cl.
*G06K 9/00*         (2006.01)
*G06T 7/187*        (2017.01)
(Continued)

(52) U.S. Cl.
CPC .............. *G06T 7/187* (2017.01); *A61B 6/032* (2013.01); *A61B 6/504* (2013.01); *A61B 6/481* (2013.01);
(Continued)

(58) Field of Classification Search
CPC ......... G06T 7/187; G06T 7/11; G06T 7/0012; G06T 7/155; G06T 7/002; G06T 7/12;
(Continued)

(56) References Cited

U.S. PATENT DOCUMENTS

| 6,842,638 B1 * | 1/2005 | Suri | ................. | A61B 6/481 |
| | | | | 382/128 |
| 2003/0031351 A1 * | 2/2003 | Yim | ................. | G06K 9/4638 |
| | | | | 382/130 |

(Continued)

OTHER PUBLICATIONS

Official Communication issued in International Patent Application No. PCT/EP2017/070150, dated Sep. 27, 2017.
(Continued)

*Primary Examiner* — Jose L Couso
(74) *Attorney, Agent, or Firm* — Stinson LLP

(57) ABSTRACT

A method and system for automatically detecting systemic arteries in arbitrary field-of-view computed tomography angiography (CTA) includes fully-automatically analyzing a medical image represented by a digital image representation.

8 Claims, 6 Drawing Sheets

(51) Int. Cl.
*A61B 6/03* (2006.01)
*A61B 6/00* (2006.01)

(52) U.S. Cl.
CPC ............. *G06T 2207/10081* (2013.01); *G06T 2207/30101* (2013.01); *G06T 2207/30172* (2013.01)

(58) Field of Classification Search
CPC .. G06T 7/143; G06T 7/62; G06T 7/60; G06T 15/08; G06T 19/00; G06T 2200/14; G06T 2207/10081; G06T 2207/30101; G06T 2207/30172; G06T 2207/20012; G06T 2207/20076; G06T 2207/20081; G06T 2207/30048; G06T 2207/30061; G06T 2210/41; G06T 2211/404; A61B 6/032; A61B 6/504; A61B 6/481; A61B 5/02007; A61B 5/489; G06K 9/4614; G06K 9/4642; G06K 9/6247; G06K 9/6282; G06K 9/6276; G06K 9/6215; G06K 9/00201; G06K 9/4638; G06K 2209/05; G06K 2209/055; G16H 30/40; G06F 19/321

See application file for complete search history.

(56) References Cited

U.S. PATENT DOCUMENTS

| | | | | |
|---|---|---|---|---|
| 2003/0053697 | A1* | 3/2003 | Aylward | G06T 7/64 382/203 |
| 2004/0249270 | A1* | 12/2004 | Kondo | G06T 7/12 600/425 |
| 2005/0110791 | A1* | 5/2005 | Krishnamoorthy | G06T 7/149 345/419 |
| 2008/0219530 | A1* | 9/2008 | Levanon | A61B 6/504 382/130 |
| 2010/0296709 | A1* | 11/2010 | Ostrovsky-Berman | G06T 7/11 382/128 |
| 2014/0355858 | A1* | 12/2014 | O'Dell | G06T 7/11 382/131 |
| 2014/0378850 | A1* | 12/2014 | Plakas | A61B 5/7275 600/504 |
| 2015/0356734 | A1* | 12/2015 | Ooga | A61B 6/5217 382/131 |
| 2016/0239956 | A1* | 8/2016 | Kang | A61B 6/032 |

OTHER PUBLICATIONS

Xiao et al., "Multiscale Bi-Gaussian Filter for Adjacent Curvilinear Structures Detection With Application to Vasculature Images", IEEE Transactions on Image Processing, vol. 22, No. 1, Jan. 2013, pp. 174-188.

Law et al., "Three Dimensional Curvilinear Structure Detection Using Optimally Oriented Flux", Computer Vision-ECCV, Part IV, LNCS 5305, 2008, pp. 368-382.

Benmansour et al., "Tubular Geodesics using Oriented Flux: An ITK Implementation", Insight Journal, Release 0.00, Feb. 1, 2013, pp. 1-8.

Schaap et al., "Standardized evaluation methodology and reference database for evaluating coronary artery centerline extraction algorithms", Elsevier, Medical Image Analysis, vol. 13, No. 5, Jun. 11, 2009, pp. 1-14.

Friman et al. "Coronary Centerline Extraction Using Multiple Hypothesis Tracking and Minimal Paths", Insight Journal, Release 1.00, Jul. 8, 2008, pp. 1-8.

Szymczak, "Vessel tracking by connecting the dots", Insight Journal, Release 0.00, Aug. 8, 2008, pp. 1-8.

Zambal et al., "Shape and Appearance Models for Automatic Coronary Artery Tracking", Insight Journal, Release 0.22, Aug. 11, 2008, pp. 1-8.

Frangi et al., "Model-Based Quantitation of 3-D Magnetic Resonance Angiographic Images", IEEE Transactions on Medical Imaging, vol. 18, No. 10, Oct. 1999, pp. 946-956.

Frangi et al., "Three-Dimensional Model-Based Stenosis Quantification of the Carotid Arteries from Contrast-Enhanced MR Angiography", Mathematical Methods in Biomedical Image Analysis, IEEE Computer Society Press, 2000, pp. 1-9.

Cohen et al., "Global Minimum for Active Contour Models: A Minimal Path Approach", International Journal of Computer Vision, vol. 24, No. 1, 1997, pp. 57-78.

Gülsün et al., "Robust Vessel Tree Modeling", Medical Image Computing and Computer Assisted Intervention, Imaging and Visualization, Part 1, 2008, pp. 602-611.

Breitenreicher et al., "Hierarchical Discriminative Framework for Detecting Tubular Structures in 3D Images", Information Processing in Medical Imaging, 2013, pp. 328-339.

Benmansour et al., "Tubular Structure Segmentation based on Minimal Path Method and Anisotropic Enhancement", International Journal of Computer Vision, vol. 92, No. 2, 2011, pp. 1-29.

Shahzad et al., "Automated extraction and labelling of the arterial tree from whole-body MRA data", Elsevier, Medical Image Analysis, vol. 24, 2015, pp. 28-40.

Lidayová et al., "Fast vascular skeleton extraction algorithm", Elsevier, Pattern Recognition Letters, 2015, pp. 1-9.

Grünauer, "Coronary Artery Tracking with Rule-based Gap Closing", Faculty of Informatics, XP055338815, Jan. 1, 2011, 104 pages.

Bauer et al., "Edge Based Tube Detection for Coronary Artery Centerline Extraction", Release 1.00, Institute for Computer Graphics and Vision, XP055338822, Jul. 22, 2008, pp. 1-8.

Kumar et al., "3D multiscale vessel enhancement based centerline extraction of blood vessels", ResearchGate, Proceedings of SPIE—The International Society for Optical Engineering, XP055209000, Mar. 13, 2013, 10 pages.

\* cited by examiner

METHOD FOR AUTOMATICALLY DETECTING SYSTEMIC ARTERIES IN ARBITRARY FIELD-OF-VIEW COMPUTED TOMOGRAPHY ANGIOGRAPHY (CTA)

CROSS REFERENCE TO RELATED APPLICATIONS

This application is a 371 National Stage Application of PCT/EP2017/070150, filed Aug. 9, 2017. This application claims the benefit of European Application No. 16183554.1, filed Aug. 10, 2016, which is incorporated by reference herein in its entirety.

BACKGROUND OF THE INVENTION

1. Field of the Invention

The present invention relates generally to the field of medical imaging and more specifically to the field of automated vessel detection. It relates to the automatic detection of systemic arteries in an arbitrary field-of-view computed tomography angiography (CTA) by means of an analysis of medical image represented by a digital image representation.

2. Description of the Related Art

Peripheral arterial disease (PAD) is a common disease which causes stenosis of non-cerebral and non-coronary arteries. It has a worldwide prevalence of around 10% in general and 15-20% in people over 70 years. Globally, 202 million people were living with PAD in 2010. Computed Tomography Angiography (CTA) is one of the non-invasive and popular techniques for imaging the arterial tree and diagnosing stenosis where arteries have a bright appearance through the injected contrast media. The non-uniform intensity appearance, similarity to bone, anatomical variations and artefacts make the artery extraction task challenging. Therefore, computer-aided artery centerline extraction tools are of high demand to assist and accelerate the extraction and analysis of the arterial tree.

In summary an artery centerline extraction framework needs to cope with the following important requirements:

1—Imaging variations: The method should be able to process images produced by imaging devices from different vendors with possible contrast inhomogeneity, different spatial resolution, noise and artefacts. In particular, vessel assessment on CTA can be limited due to multiple problems including cardiac and aortic pulsations, beam-hardening artefacts from vessel wall calcifications, poor contrast opacification of vessel lumen due to inadequate contrast dose, vessel stenosis and other reasons.

2—Anatomical variations: The method should cope with vessels that may vary considerably in shape, sizes and curvature depending on anatomy and presence of pathologies.

3—Timing performance: The method should be, when implemented on contemporary computer infrastructure, executable in a reasonable time which is a challenging requirement since complete analysis of a vascular network is computationally demanding, mainly due to a huge search space.

Most vessel analysis related techniques can be subdivided into three main categories and may be used in combination with each other: vessel enhancement, vessel segmentation and centerline extraction. Vessel enhancement algorithms often act as a constituent step in more sophisticated pipeline algorithms including vessel centerline extraction and segmentation. Centerline extraction algorithms in their turn usually allow for a further reconstruction of the whole object, therefore often making a part of vessel segmentation pipeline algorithms.

1) Vessel enhancement: These techniques are usually centered on a so-called tubeness or vesselness measure, representing the probability of being a vessel (or being a point within a vessel). Optimal edge detection, intensity ridge detection methods steerable filters and Hessian-based methods have been widely used for enhancement of tubular structures in medical images. Hessian-based methods are among the most popular and best performing ones of all kinds of vesselness-centered approaches.

In most vesselness-related methods eigenvalues of Hessian matrices are computed first and then combined together into vesselness measures. Different combinations of eigenvalues enhance tubular, plate-like or blob-like structures. Hessian matrices are typically approximated by Gaussian derivatives. Xiao et al. [C. Xiao, M. Staring, Y. Wang, D. P. Shamonin, and B. C. Stoel, "Multiscale bi-gaussian filter for adjacent curvilinear structures detection with application to vasculature images." IEEE Transactions on Image Processing, vol. 22, no. 1, pp. 174-188, 2013.] proposed to replace the kernel with a bi-Gaussian function to allow for independent scale selection in both foreground and background. Optimally oriented Flux (OOF) has been introduced by Law and Chung [M. W. Law and A. C. Chung, "Three dimensional curvilinear structure detection using optimally oriented flux," in Computer Vision-ECCV 2008. Springer, 2008, pp. 368-382.] to overcome some of the drawbacks of Hessian-based algorithms for segmentation of vessels [F. Benmansour, E. Turetken, and P. Fua, "Tubular geodesics using oriented flux: an itk implementation," Tech. Rep., 2013.].

Despite that Hessian-based methods and OOF show a greatly enhanced performance they are computationally very expensive especially in large volumetric scans, and this mainly due to the costly procedures required to obtain filter responses.

2) Centerline extraction/tracking: In many medical applications description of vascular networks based on extracted centerlines is an essential pre-processing step. In such cases tubular structures or vessels in particular, are represented by medial lines which are quite often accompanied by estimated geometric features (such as the radius of a vessel) at their constituent points. Classic centerline extraction approaches include direct tracking methods, model-based optimization methods and minimal path techniques. Most of such centerline extraction algorithms are semi-automated and usually require user interaction. The potential of such methods was validated during the segmentation challenge workshop in the Medical Image Computing and Computer-Assisted Intervention (MICCAI) conference in 2008 [M. Schaap, C. T. Metz, T. van Walsum, A. G. van der Giessen, A. C. Weustink, N. R. Mollet, C. Bauer, H. Bogunovi'c, C. Castro, X. Deng et al., "Standardized evaluation methodology and reference database for evaluating coronary artery centerline extraction algorithms," Medical image analysis, vol. 13, no. 5, pp. 701-714, 2009.]. 13 coronary artery centerline extraction methods participated in the challenge. The leading methods were introduced by Friman et al. [O. Friman, C. Kuehnel, and H. Peitgen, "Coronary centerline extraction using multiple hypothesis tracking and minimal paths," 07 2008.], Szymczak et al. [A. Szymczak, "Vessel tracking by connecting the dots," The Insight Journal, 2008.] and Zambal et al. [S. Zambal, J. Hladuvka, A. Kanitsar, and K. Buhler, "Shape and appearance models for automatic coronary artery tracking," in Proc. Of MICCAI Workshop 3D Segmentation in the Clinic: A Grand Challenge II, 2008.]. Most direct tracking methods require one seed point at the root of the vascular tree. Tracking usually progresses along the vessel starting from the given seed point. Successive centerline positions are estimated at each step depending on the surrounding geometric or image-based features.

Model-based optimization methods require start and end points for every given vascular segment. In works by Frangi et al. [A. F. Frangi, W. J. Niessen, R. M. Hoogeveen, T. Van Walsum, M. Viergever et al., "Model-based quantitation of 3-d magnetic resonance angiographic images," Medical Imaging, IEEE Transactions on, vol. 18, no. 10, pp. 946-956, 1999.] and [A. F. Frangi, W. J. Niessen, P. J. Nederkoorn, O. E. Elgersma, M. Viergever et al., "Three-dimensional model-based stenosis quantification of the carotid arteries from contrast-enhanced MRA," in Mathematical Methods in Biomedical Image Analysis, 2000. Proceedings. IEEE Workshop on. IEEE, 2000, pp. 110-118.] spline deformable models have been applied for optimizing a centerline model with fixed boundary conditions.

Minimal-path techniques are commonly employed in an interactive manner requiring the definition of start and end points for each target vessel. In such algorithms, the centerline points for which a specific energy function reaches its minimum are extracted. Cohen and Kimmel [L. D. Cohen and R. Kimmel, "Global minimum for active contour models: A minimal path approach," International journal of computer vision, vol. 24, no. 1, pp. 57-78, 1997.] modified the "snake" energy by including the internal regularization term in the external potential term. A path of minimal length is found numerically then in a Riemannian metric. Other techniques differ usually in the numerical optimization schemes they use. Graph-based schemes by Gulsun et al. [M. A. GUlsun and H. Tek, "Robust vessel tree modeling," in Medical Image Computing and Computer-Assisted Intervention-MICCAI 2008. Springer, 2008, pp. 602-611.] and Breitenreicher et al. [D. Breitenreicher, M. Sofka, S. Britzen, and S. K. Zhou, "Hierarchical discriminative framework for detecting tubular structures in 3d images," in Information Processing in Medical Imaging. Springer, 2013, pp. 328-339.] employ discrete Dijkstra-like modifications. Benmansour and Cohen [F. Benmansour and L. D. Cohen, "Tubular structure segmentation based on minimal path method and anisotropic enhancement," International Journal of Computer Vision, vol. 92, no. 2, pp. 192-210, 2011.] use the minimal path method and anisotropic fast-marching with a metric based on OOF [M. W. Law and A. C. Chung, "Three dimensional curvilinear structure detection using optimally oriented flux," in Computer Vision-ECCV 2008. Springer, 2008, pp. 368-382.]. The model takes geometric features of the vessel such as width and orientation into account. The algorithm has been tested on synthetic and real 2D and 3D images.

However, there exist only few algorithms which could be roughly compared with the method proposed in this application in terms of applicability to multiple parts of the human body and/or large 3D CTA scans. We have found only one fully-automated method able to extract a 3D arterial tree from multiple parts of the human body. Shahzad et al. [R. Shahzad, O. Dzyubachyk, M. Staring, J. Kullberg, L. Johansson, H. Ahlstrm, B. P. Lelieveldt, and R. J. van der Geest, "Automated extraction and labelling of the arterial tree from whole-body MRA data," Medical Image Analysis, vol. 24, no. 1, pp. 28-40, 2015.] presented a fully automated algorithm for extraction and labelling of the arterial tree from whole-body magnetic resonance angiography (WB-MRA) sequences. Lidayova et al. [K. Lidayová, H. Frimmel, C. Wang, E. Bengtsson, and Ö. Smedby, "Fast vascular skeleton extraction algorithm," Pattern Recognition Letters, 2015.] proposed a fast skeleton extraction algorithm in 3D CTA scans of the lower limbs. Great accuracy rates have been demonstrated in both methods. In the former method referenced above though, it is not clear whether it could be easily adapted to other imaging modalities such as CTA, or to for instance cropped data or different field-of-view scans. In the latter method referenced above, it is not obvious whether the method could be easily expanded to the other parts of the human body. Besides it has been tested only on the scans with no veins being visible. In both cases the authors have not reported centerline accuracy values.

Andreas Grünauer: "Coronary Artery Tracking with Rule-based Gap Closing", (1 Jan. 2011 (2011-01-01), XP055338815, Retrieved from the Internet: https://publik-.tuwien.ac.at/files/PubDAt_201145.pdf) discloses an approach that is divided into three phases: 1) calculation of seed points, 2) tracking of vessel segments, and 3) construction of the coronary artery trees. Phase 1 & 2 are executed in an automatic manner. First potential seed points for the tracking of vessel segments are identified. During the second phase, vessel segments located at these seed points are tracked by use of a cylindrical shape model. By use of rule-based anatomical heuristics, the third and final phase combines vessel segments to form complete coronary artery trees. This phase requires minimal user interaction, as the location of the root of the left and right coronary artery tree needs to be specified.

The method proposed in this application addresses the above-listed requirements and overcomes certain drawbacks encountered in the methods referred to above. The method described here does not depend on a particular image intensity contrast and is therefore completely transparent to variations in imaging characteristics.

SUMMARY OF THE INVENTION

The present invention provides a method for analyzing a slice-based scanned image volume of a body represented by a digital image representation comprising the steps of: determining to which body region the slice-based scanned image volume belongs, determining the expected vessel characteristics for occurring vessels in said body region, said characteristics comprising vessel radii, relative distance parameter thresholds, vessel intensity value thresholds and anatomy-driven vessel segment connection rules, determining seed points in said image volume representing centers of vessels, tracking of unconnected vessel segments with said seed points as the starting point by iteratively determining subsequent neighbouring seed candidates which are selected based on a value which represents the likeliness for a point (of a slice based representation) belonging to a vessel, iteratively extending a vessel tree by connecting said unconnected vessel segments, applying a set of connection rules on said unconnected vessel segments in each iteration step, terminating the iteration when none of a set of connection rules is fulfilled anymore.

The above-described aspects are solved by a method as set out below.

In the context of this invention, the scanned image volume can apply to an imaged volume of a part of the patient volume (and thus representing only a part of the full body) or of the entire patient volume. The scanned image volume thus does not need to include the outer patient contours, and in other words may be truncated.

The body regions referenced in this application refer to slice ranges of body parts relevant for the detection of blood vessels; and more specifically to the abdominal aortic region (AO), the aortic arch (AOA), the left and right carotid arterial region (LCC and RCC) and the left and right iliac aortic part of the body (LCI and RCI). Blood vessels can be assigned well-determined characteristics (such as the minimum and maximum estimated vessel radii encountered in said body region) which can be further used as parameters in the subsequent steps of the imaging pipeline.

A seed point has to be interpreted as a well determined point in the scanned image volume which can be considered to be a confirmed point representing an element of an identified blood vessel. A seed point is then used as a starting point for a subsequent method step to detect the remainder of the vessel segment.

The relative distance parameter is in the context of this application a measure for circularity of a vessel at a given position. Small values close to zero correspond to approximately circular structures.

A vesselness value is the result of a vesselness function calculated for a given location. The vesselness function calculates the likeliness for a location or point to belong to a vessel-like structure. Detailed description of an embodiment of a vesselness function is provided further down in the detailed description of this application.

The embodiments of the systems and methods described herein may be implemented in hardware or software, or a combination of both. However, preferably, these embodiments are implemented in computer programs executing on programmable computers each comprising at least one module component which comprises at least one processor (e.g. a microprocessor), a data storage system (including volatile and non-volatile memory and/or storage elements), at least one input device, and at least one output device. For example and without limitation, the programmable computers (referred to here as computer systems) may be a personal computer, laptop, personal data assistant, and cellular telephone, smart-phone device, tablet computer, and/or wireless device. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The subject system may also be considered to be implemented as a computer-readable storage medium, configured with a computer program, where the storage medium so configured causes a computer to operate in a specific and predefined manner to perform the functions described herein.

Specific examples and preferred embodiments are set out below.

The method disclosed in this application has a multiscale approach and is able to detect vessels of a broad range with sizes ranging from very large primary vessels such as aorta to the very small secondary ones. In addition to that, the method is able to track vessels even in problematic cases in presence of calcifications and stenosis. The method disclosed allows implementation into semi- and fully-automated detection appliances where both perform in a reasonable time and reach similar high accuracy rates. To the best of our knowledge, the method described here is the first fully-automated method able to extract centerlines and radius information in multiple parts of the human body in arbitrary field-of-view 3D CTA scans.

The main differences provided by this invention in comparison with described methods in the art are that:
- the described method is a semi- or fully-automated framework for arterial tree reconstruction independently of the part of the human body it is applied to, and independently from the field-of-view.
- body part detection and vessel regression methods have been introduced as integral parts of the semi- or fully-automated frameworks.
- anatomy-driven connection rules for the tree growing algorithm have been introduced in order to ensure anatomically correct vessel trees.
- a continuous genetic algorithm is used to optimize values for body-part specific parameters.

The present invention is beneficial in that the aforementioned accuracy and speed can be achieved when implemented on a standard computer platform. Besides this, the described method is the only method known so far which can be applied in a fully automated way. Moreover, the method is capable of processing scanned image volumes which cover a limited field of view of a patients' body, whereas previously described methods required that the external contours of the body would be visible in the image volume in order to ensure successful processing.

Further advantages and embodiments of the present invention will become apparent from the following description.

DETAILED DESCRIPTION OF THE PREFERRED EMBODIMENTS

Figure 1:
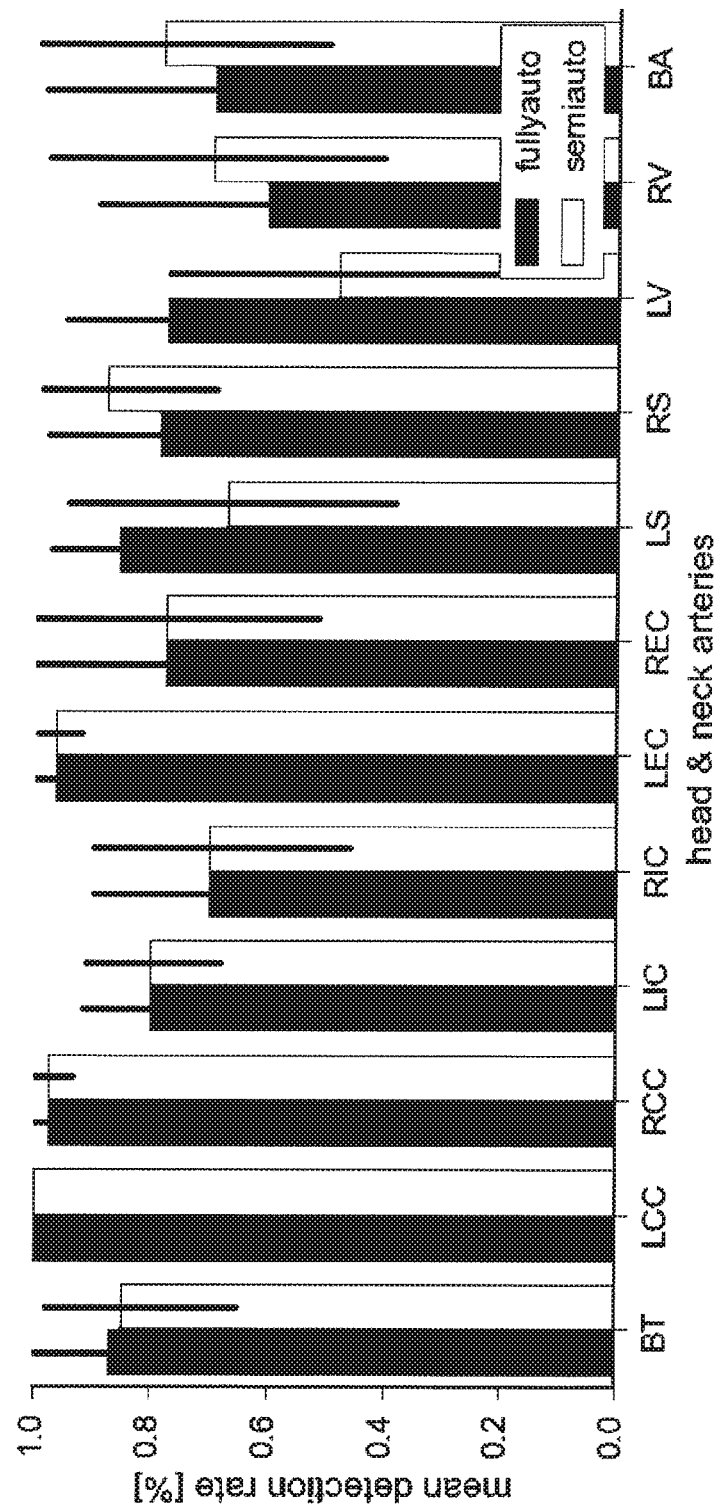
FIG. 1 shows the detection rates for head & neck arteries from the test dataset Collection 1.
Figure 2:
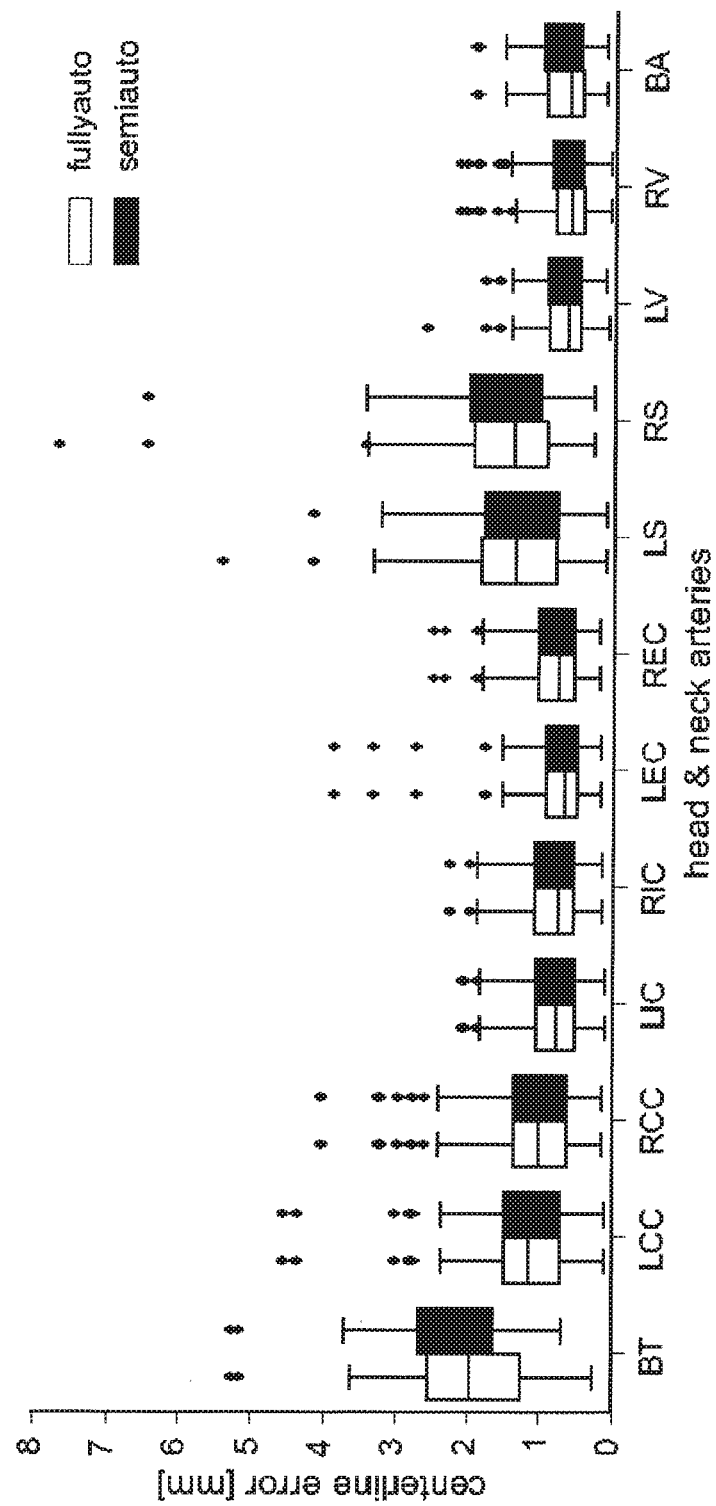
FIG. 2 shows the centerline errors for head & neck arteries from the test dataset Collection 1.
Figure 3:
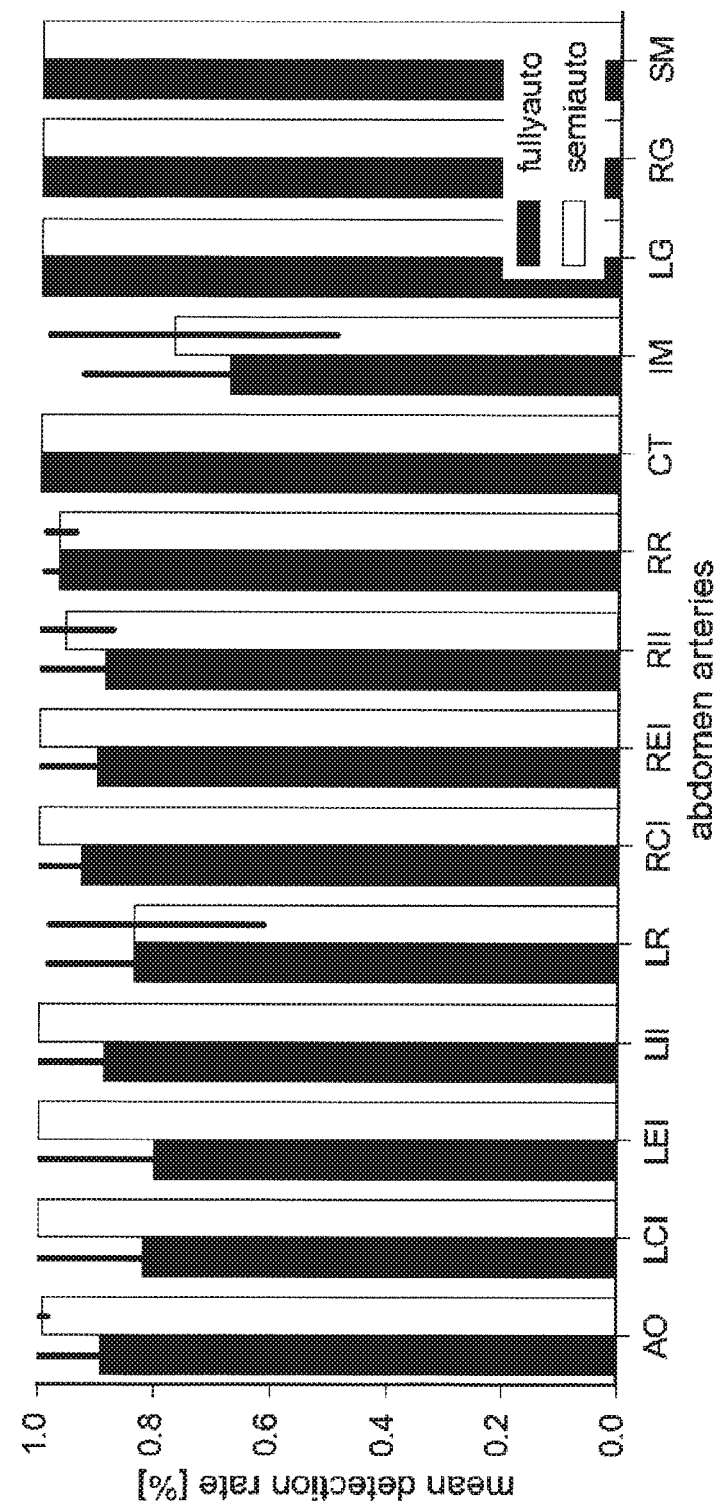
FIG. 3 shows the detection rates for abdominal arteries from the test dataset Collection 1.
Figure 4:
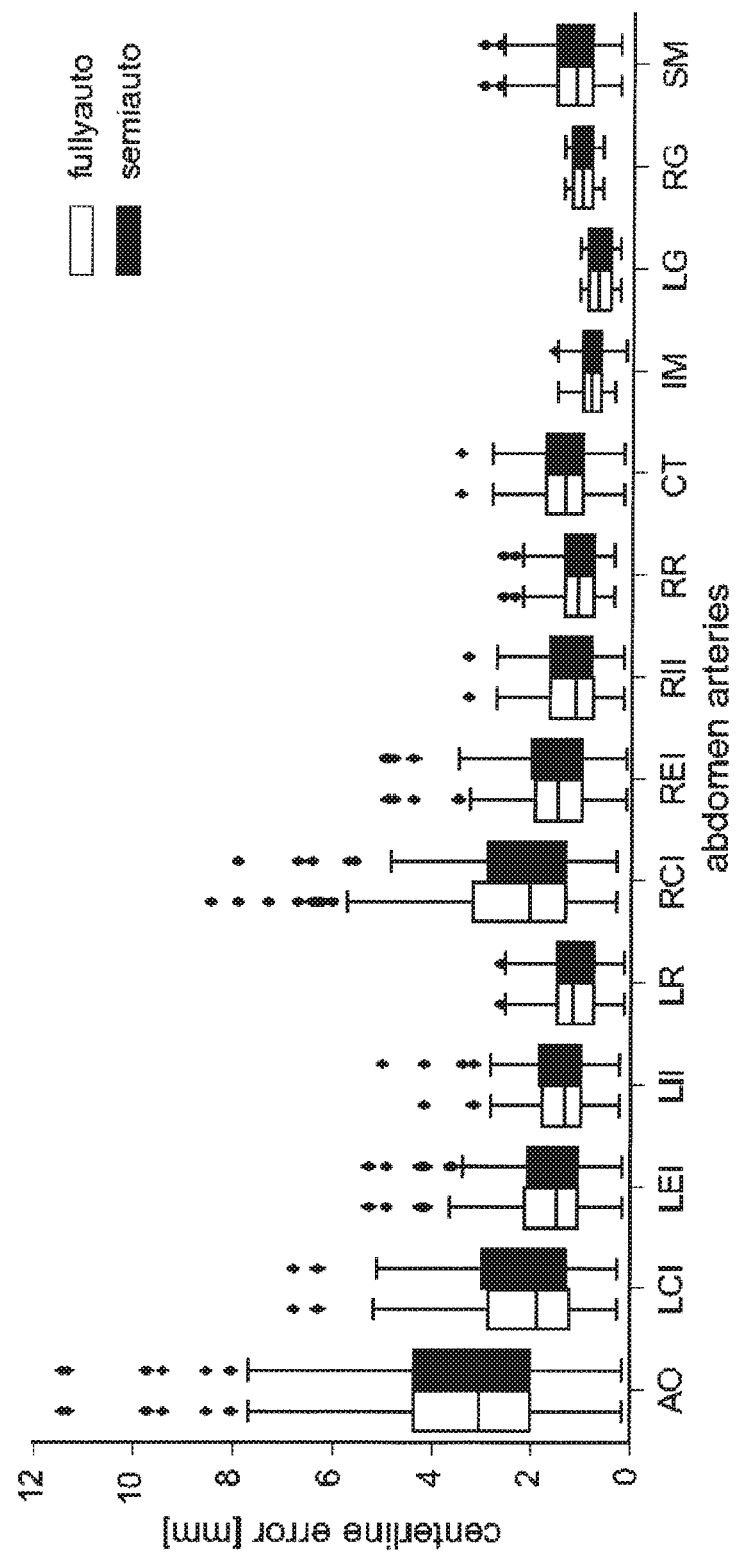
FIG. 4 shows the centerline errors for abdominal arteries from the test dataset Collection 1.
Figure 5:
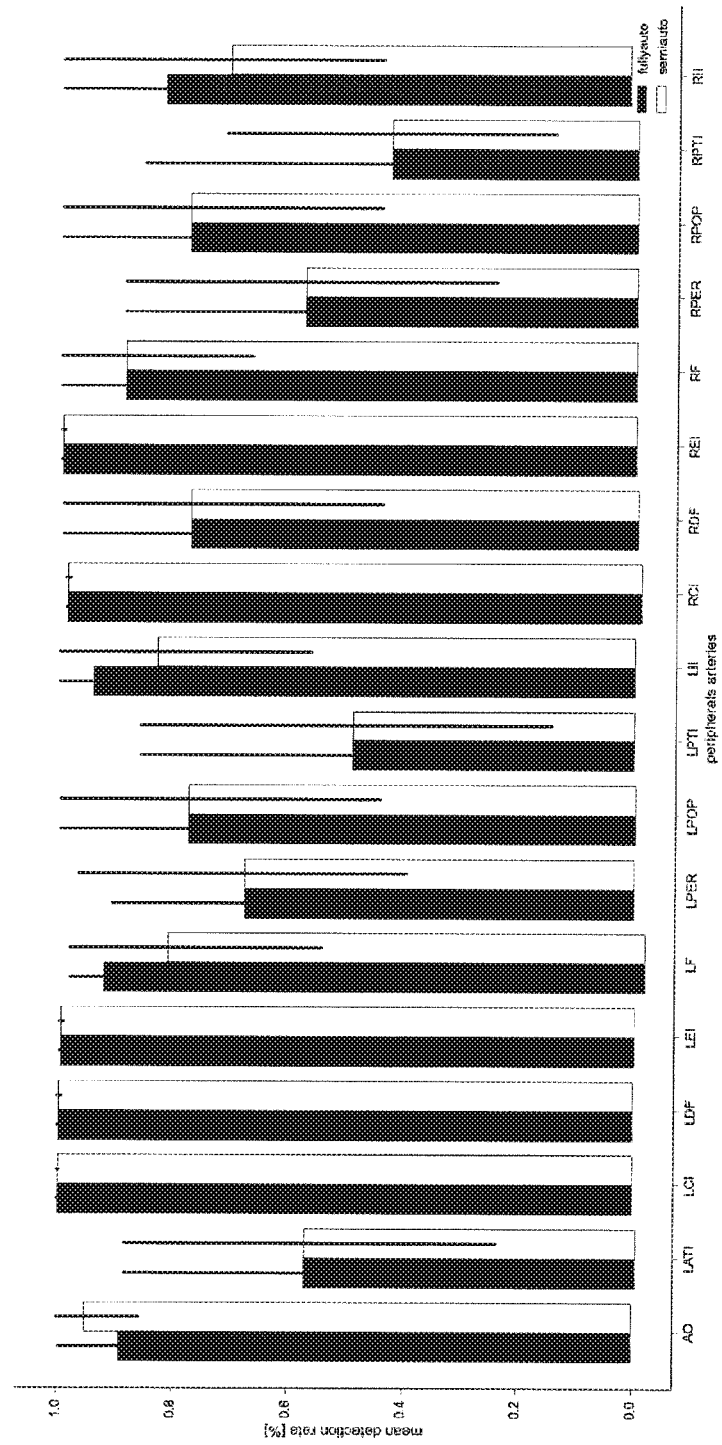
FIG. 5 shows the detection rates for peripheral arteries from the test dataset Collection 1.
Figure 6:
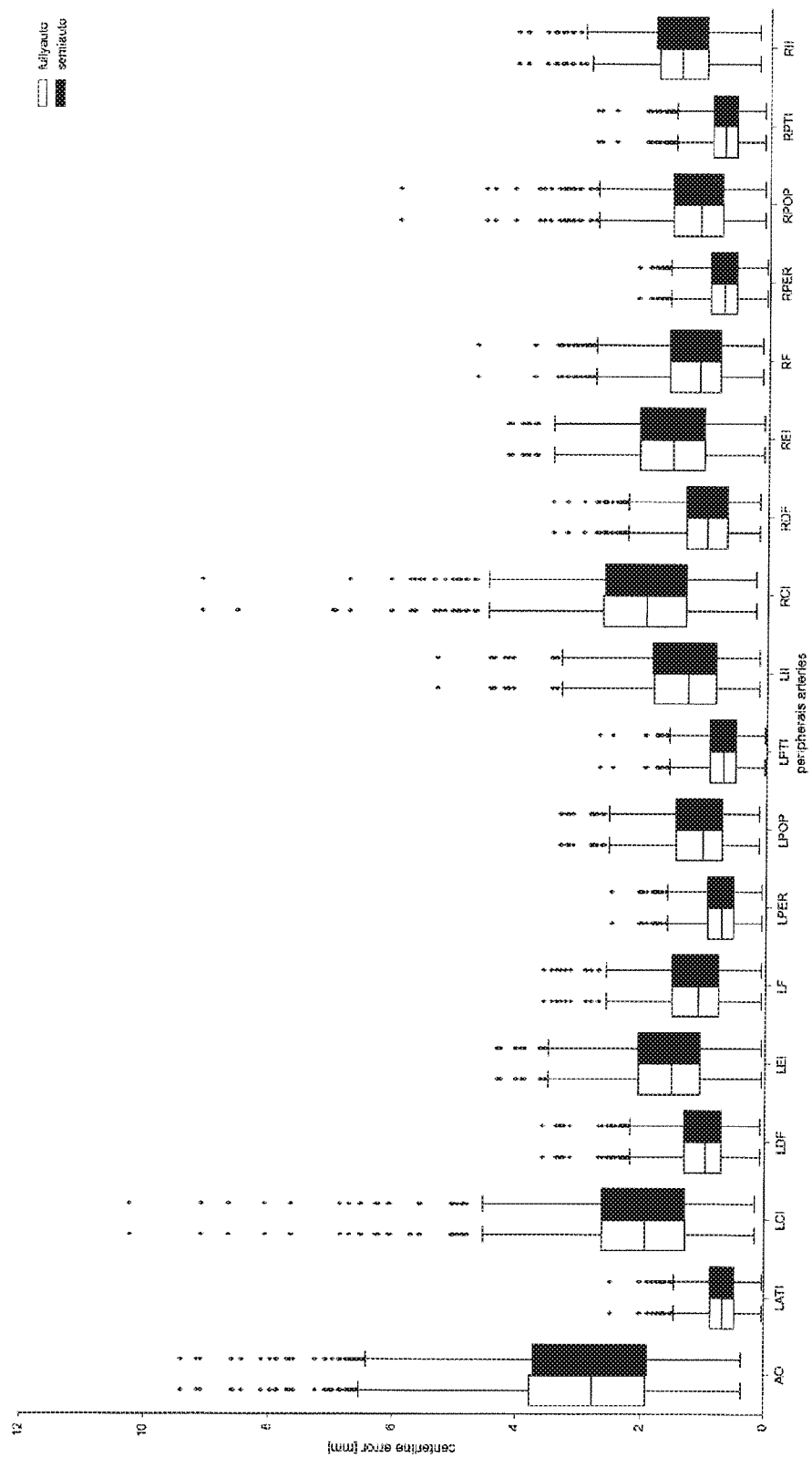
FIG. 6 shows the centerline errors for peripheral arteries from the test dataset Collection 1.

In the following detailed description, reference is made in sufficient detail to practice the embodiments explained below by those skilled in the art.

Arteries vary in diameter and length depending in their position in the human body. More than that, the geometry of arterial tree parts differs from one body region to another. For that reason in one embodiment of our invention, the vessel tracking framework starts with detection of the body region of the CTA (computed tomography angiography) scan and adjusts the further steps accordingly. Major vessel detection performance improvements have been proven which can be attributed to the implementation of this body region detection as a first step. Possible vessel seed positions in the whole scan are detected at the next step. Underlying vessel structures are then tracked via vessel model matching starting from the seed positions. The tracked segments are finally connected to an arterial tree by a tree growing algorithm from an initial position. The tree growing step uses specific parameters to body regions and is initialized either manually or automatically.

As a first step, the body region detection step is disclosed. In order to recognize a body region and the main arteries present in the CTA scanned volume V, a slice-based regression approach proposed by Major et al. [D. Major, A. Novikov, M. Wimmer, J. Hladuvka, and K. Buhler, "Automated slice-based artery identification in various field-of-view CTA scans," in Eurographics Workshop on Visual Computing for Biology and Medicine, VCBM 2015, Chester, UK, Sep. 14-15, 2015., pp. 123-129.] is used in the method described here, however different methods may be envisaged.

As a first step the position of each slice $j \in N$ is predicted in a global standardized body space $h: N \to [0,1]$ where the position of the toes (of the human body) correspond to the position $h(j)=0$ and the top of the head to $h(j)=1$. The global standard body space position of each slice is related to the tissue composition captured by a regression model. Additionally, slice ranges for body parts from $$\mathcal{B} = \{AO, AOA, LCC, RCC, LCI, RCI\}$$

are learned in the h-space using deep learning techniques. AO is the abdominal aortic region, AOA the aortic arch, LCC and RCC the carotid arterial region and LCI, RCI the iliac arterial part of the body.

After regressing each slice's h-mapped position, the information on which body parts are present in the scan is derived. Furthermore, the algorithm learns a function G defined as:

$$\mathcal{G}(\kappa) = (o_1, o_2), \kappa \in h, (o_1, o_2) \in \mathbb{R}^2_{>0}$$

which maps the slices' h-positions into pairs of their typical estimated minimal and maximal radii. Slice ranges and the function G build an essential input for the following steps of the pipeline.

As a second step, the seed detection step is disclosed. Other seed detection methods besides the one described here, may be envisaged as well. This step produces initial approximate locations of vessel-like structures in the volume as an output. At good positions, possibly being within the vessel-like structures, directional vectors and radii are estimated. A triplet $c = (p_c, \vec{v}_c, r_c)$ consisting of position $p_c$, vector $\vec{v}_c$ and radius $r_c$, defines a seed candidate. Bad seed candidates are filtered out. The good ones are passed then to the next step of the method.

The seed detection step is achieved by seed candidate pre-selection and subsequent seed filtering.

The seed candidate pre-selection assumes that the vessels are bright structures with high local symmetry usually surrounded by darker (soft tissue) or much brighter structures (in case of bone); all positions in the volume V with intensity level lower then a minimal acceptable threshold are discarded. At the next step, the method aims to find edges of vessel-like structures. To achieve that, the positions with the magnitude of the gradient $\nabla I > M_{min}$ are selected. Two opposite neighbouring positions along the gradient direction $\vec{g}$ of a given position $p_0$ are selected, and their average intensity level $I_{avg}$ is calculated. A ray is sent in the gradient direction until a position with intensity level $< I_{avg}$ is hit. The distance $\lambda_0$ to the starting position $p_0$ is calculated. At every pre-selected position the radius $r_c$ of a candidate seed is taken as $\lambda_0/2$. The position $p_c$ in the center of the vessel-like structure is defined using the position $p_0$ and the normalized gradient vector $$p_c = p_0 + r_c \frac{\vec{g}}{\|\vec{g}\|}$$

In order to analyze the geometrical properties of the vessel-like candidate object around the $p_c$, the parametric form of the longitudinal plane perpendicular to the gradient $\vec{g}$ is derived through finding a pair of orthonormal vectors $\vec{w}_0$ and $\vec{w}_1$ spanning the plane.

Subsequent seed filtering is performed by removing false seed candidates in the plane defined by the basis formed by $\vec{w}_0$ and $\vec{w}_1$, $N_r$ equidistant radial rays with directions set by unit vectors $\vec{\xi}_k \in \mathfrak{R}$ are sent from the central point $p_c$ until positions with intensity levels falling below the estimated threshold $I_{avg}$ are hit. Such positions form a contour set L:

$$L = \{p_k | p_k = p_c + \lambda_k \cdot \vec{\xi}_k \wedge I(p_k) < I_{avg}\}$$

where $k \in \mathbb{N}^*_{\leq N_r}$ and $\lambda_k = \|p_k - p_c\|$.

To approximately evaluate the circularity at a given position within a vessel-like structure in its traverse cross-section, the relative distance parameter $D^r$ is introduced. Small values of this parameter (close to zero) correspond to approximately circular structures.

A candidate is not further processed if its $D^r$ exceeds the maximal acceptable relative distance $D_{max}^r \in (0,1)$:

$$D^r = \left| \frac{\lambda_{min}}{r_c} - 1 \right| > D_{max}^r$$

In the case that the equation above holds, then the candidate with position $p_c$ and the radius $r_c$ is taken as a candidate for being within a vessel-like structure.

Since it is the purpose of the method to identify vessels with diameters of real anatomical sizes in the considered part of the body, the function $\mathcal{G}(\bullet)$ which is learned during the body part detection step, is used for a final check to remove candidates that do not fulfil $v_{min} < r_c < v_{max}$, where $(v_{min}, v_{max}) = \mathcal{G}(h(z_c))$, $z_c$ being the closest slice height to the point $p_c$ and $h(z_c)$ is the h-mapped position of the slice height $z_c$.

The direction of the candidate seed is defined then as a normalized cross-product of the gradient $\vec{g}$ and the translation vector from the point $p_c$ to the point $p_{min} \in \mathcal{L}$. Candidate positions that fulfill all above-mentioned criteria form a set of triples:

$$S := \{(p_i, \vec{v}_i, r_i) : p_i \in V, \vec{v}_i \in U, r_i \in \mathbb{R}_{>0}\}$$

where $\mathcal{U} := \{\vec{v} : \vec{v} \in \mathbb{R}^3 \wedge \|\vec{v}\| = 1\}$.

As a third step, the segment tracking step is disclosed. In order to detect potential vessel-like segments in the volume V, the seeds estimated in the previous step of the pipeline are used as initialisation to a modified version of the algorithm proposed by Zambal et al. ["Shape and appearance models for automatic coronary artery tracking", in Proc. Of MIC-CAI Workshop 3D Segmentation in Clinic: A Grand Challenge II, 2008."] which has been proven to show very good performance. Other methods may however be envisaged as well. The difference to the original algorithm referenced above is that the disclosed segment tracking step does not follow the depth-first search strategy in order to connect the tracked segments at the same time, but rather tracks one segment per seed candidate and delegates the tree building procedure to the next step of the disclosed method.

During the segment tracking step, a centerline is extracted by an iterative matching of a rigid symmetric model until geometry and intensity-based termination criteria are met. For each candidate a so-called "vesselness function" calculates the likeliness of belonging to a vessel-like structure. Selected successive candidates form a vessel segment. Selecting the successive candidates is achieved through bi-directional tracking.

The estimation of the vesselness is achieved through a method fully described by Zamal et al. (see above) and which comes down to a method where at each given candidate $(p_k, \vec{v}_k, r_k)$ a histogram-based function is estimated. Texture samples are generated by using two shape patterns (used for two different levels of detail) consisting of two concentric circles which are translated and scaled along direction $\vec{v}_k$.

The bi-directional tracking method starts at some candidate $c \in S$ and proceeds in two opposite directions and explores as far as possible along each direction. At each position following candidates are generated, and the one with the most similar shape configuration and best fitting vesselness value is taken as the successor.

Given a candidate $c=(p_c, \vec{v}_c, r_c)$, a set of following candidates is generated as follows. Direction vectors $\vec{v}_i$ deviating from $\vec{v}$ at elevation angles $\alpha \in [\alpha_{min}, \alpha_{max}]$, azimuth angle $\beta \in [\beta_{min}, \beta_{max}]$, and elevation angle increment $\Delta\alpha$ are generated and positions for the succeeding candidates are calculated then as $p_i = p_c + \delta(\vec{v} + \vec{v}_i)/2$, where the step size $\delta = r_c (1+A(\alpha))/2$ and $\alpha$ is the angle between $\vec{v}_c$ and $\vec{v}_i$.

The angular function $A(\alpha)$ defines how many candidates should be considered at each angle range for each direction:

$$A(\alpha) = \begin{cases} 6, & \text{if } \alpha < 5° \\ 3, & \text{if } 5° \le \alpha < 30° \\ 2, & \text{if } 30° \le \alpha < 60° \\ 1, & \text{else} \end{cases}$$

$A(\alpha)$ is especially important in case small intensity interruptions are present within vessels. By taking more steps in the directions with small angle deviations the algorithm would be able to jump over small intensity interruptions. Radii for the new candidates are taken iteratively from the set $$\left\{ \frac{r_c}{2}, \frac{r_c r_s}{2}, \ldots, \frac{r_c r_s^{n-1}}{2}, \min\left(\frac{r_c r_s^n}{2}, \frac{3r_c}{2}\right) \right\}$$

where $r_s > 1.0$ is the radius scaling multiplier. Angle increment and radius scaling multiplier $r_s$ define how extensive the search for the following candidates should be. The larger values of $r_s$ are the less extensive search becomes.

From all generated and evaluated triples the one $c_{opt}$ with the best vesselness function is taken further to the refinement step. To refine the candidate, a set of altered (different position, scaling, radius) candidates around $c_{opt}$ are generated. The candidate with the largest vesselness function is chosen and taken as the next candidate within the tracking procedure.

A sequence of connected triples $(p_i, \vec{v}_i, r_i)$ forms a segment set $E_j$. Each vessel segment is an undirected acyclic graph at which every vertex has one or two neighbouring triples depending if the triple is located at the end or in the middle of the segment. A segment $E_j$ is not processed further if $|E_j| < 3$.

As a fourth and final step, a vessel tree growing part of the method builds a vessel tree out of unconnected segments resulting from the previous segment tracking part of the pipeline. At the initialization point, the closest unconnected segment represents an initial vessel tree. The vessel tree is iteratively extended by connecting neighbouring unconnected segments until none of the connection rules are fulfilled anymore. The vessel tree growing step thus comprises 3 different elements; tree initialisation, the application of tree connection rules, and an iterative procedure ensuring full detection of the vessel tree. Preferably, this method is used, however other methods may be envisaged.

The tree growing part of the method may be initialized in either semi- or fully automated manner; in one embodiment if this invention a semi-automated tree growing procedure is manually initialized by giving starting positions within vessels. Proper functioning of the algorithm can be guaranteed if three positions are given for each head & neck (two positions in left and right common carotid arteries and one in aortic arch or aorta) and leg (two positions in left and right common iliac arteries, and one in aorta) scans. A single point selection on an image in the aorta is normally enough for abdominal scans.

In another embodiment, the initial positions are found automatically within key arteries by for instance applying the method proposed by Major et al. [D. Major, A. Novikov, M. Wimmer, J. Hladuvka, and K. Buhler, Automated slice-based artery identification in various field-of-view CTA scans, in Eurographics Workshop on Visual Computing for Biology and Medicine, VCBM 2015, Chester, UK, Sep. 14-15, 2015., pp. 123129.]. First, slice region $R^\theta$ covering a main artery of interest $\theta \in \{LCI, RCI, AO, AOA, LCC, RCC\}$ is detected. Second, candidates for the artery slice-positions are localized in a slice-wise manner. Positions are sampled on every slice in the region $R^\theta$ and Histogram of Oriented Gradients (HOG) features are extracted locally around them. Extracted HOG features are put in relation to the slice position of an artery of interest and this relationship is fed to a Nearest Neighbor (NN) regression model. To refine the result of the NN-regression each regressed position based on image and anatomy-context features is classified additionally between the artery of interest and the rest. Positions which compose the best and smoothest artery-like transitions across consecutive slices provide the final candidates for each artery $\theta$. The best $M_{pos}$ positions within each $\theta$ are taken as an initialization for the final tree growing step of the pipeline.

The tree growing part of the method employs two types of intersegment connections and two types of connection rules. A rule makes a decision if one or more nodes of an unconnected segment should be connected to the considered node. When two end nodes (nodes having only one neighbour) from both segments are connected to each other they are called to make up an "E-E connection" and the algorithms that use sets of connection rules to deal with such connections will be called "E-E connectors" If an end node of one segment is connected to an inner node (node with more than one neighbour) of another segment this connection is called an "E-I connection", and the algorithm responsible for this type of connection is called "E-I connector" correspondingly. For each connection type the disclosed method applies two types of connectors; shortest path- and geometry-based connectors.

Shortest path-based connectors base their decisions on smooth intensity transitions. These connectors are capable of dealing even with highly geometrically challenging connections provided that intensity transition exists and distinguishes from noise or background. Geometry-based connectors, though they mainly use relatively basic geometric information, play an important role especially in highly challenging cases when due to plaques, imaging artefacts or low contrast, intensity information is distorted.

For both types of connectors (E-E and E-I) a set of body-part specific parameters is defined to address the diversity of the anatomies in different parts of the human body, as follows:

Body Part Specific Parameters for Geometry-Based Connector:
  a) Maximal distance coefficient for two segments: $\Phi_0^b$
  b) Minimal acceptable ratio between radii of two segments: $R_{min}^b$
  c) Maximal acceptable ratio between radii of two segments: $R_{max}^b$
  d) Maximal acceptable angle between segments: $M_{max}$
  e) Maximal acceptable radii difference: $R_{avg}$ Body Part Specific Parameters for Shortest Path-Based Connector:
  a) Number of sampled intensities: M
  b) Minimal accepted Hellinger distance: $P_a$
  c) Minimal accepted deviation from Gaussian density: $P_g$
  d) Geodesic scaler for region growing connector: $W_0$ Experiments showed that default parameters $\Phi_0^b$, $R_{min}^b$ and $R_{max}^b$ are the only ones that vary significantly depending $b \in \mathcal{B}$ on the body region.

The shortest path-based connector uses a shortest-path algorithm enriched with elements of the minimal cost path algorithm. Given the source and the target nodes it aims to find a path between the nodes such that two conditions are satisfied. First, geometrically the path should not deviate much from the Euclidean path. Second, the Gaussian distributions intensities at each position along the path should be similar.

For both types of connections (E-E and E-I) the connector proceeds in a similar manner. Two distinct Gaussian distributions $N(\sigma_1,\mu_1)$ and $N(\sigma_2,\mu_2)$ are reconstructed based on M samples taken from each segment. Two segments are connected in case if the Hellinger distance $H^2(N_1,N_2)$ between distributions is low:

$$H^2(N_1,N_2) < P_a \in [0,1]$$

Finally, the algorithm attempts to reconstruct a path between two segments being as close as possible to a straight discreet line $L=\{e_p, p_1, p_2, \ldots p_m, e_c\}$ between the segments. The algorithm starts at the end position $e_p$ at the parent segment (source) with an aim to reach $e_c$ at the child segment (target).

In an iterative manner, between each point $p_i$ and the source position $e_p$ the deviation $\gamma$ of Gaussian intensity distribution is estimated. In case if $\gamma < P_g$ a new position in the 3D neighbourhood is found, and a new discreet line to the destination position $e_c$ is reconstructed. The algorithm stops when $\|p_i - e_c\| < v$.

In contrast, the geometry based connectors use angle, distance and shape-related criteria in order to connect two segments. Both E-E and E-I connectors analyze angles between tangent vectors from both segments. The angle between two vectors should not exceed a body-part dependent parameter $M_{max}$ which in its turn varies depending on the connector type, i.e. an angle for two segments in the E-I connection could be much larger than for E-E connection, since angles for E-E connections should be rather small. Allowed distance between two segments is another connection criterion. The distance between two nodes should not exceed $\Phi_0^b \cdot r_{parent}$ (wherein $\Phi_0^b$ is the maximal distance coefficient for two segment, a body-part specific parameter). To permit the connection of two segments the ratio of radii of the parent and child nodes should lie in the predefined range $\{R_{min}^b, R_{max}^b\}$. This ratio changes for different types of connections, since it is critical for the E-I types of connections that the radius of the inner node of the parent segment is larger than for the child segment.

In other embodiments, the parameters used in the connectors (or vessel connecting methods) may be optimized according to different strategies. Preferably, the following method is used.

Genetic algorithms are popular mathematical methods for optimizing non-linear systems with a large number of variables. In this disclosure we have employed a continuous genetic algorithm to find the most optimal body-part specific parameters for the geometry and shortest path-based connectors. In such a genetic algorithm, an array of parameters is represented as a so-called chromosome comprising the parameters from both types of connectors (geometry-based and shortest path-based connectors) in their body part context. Additionally a blending method is used to produce offspring chromosomes from a combination of parent chromosomes. The results of such offspring chromosomes are evaluated by comparing the final result of the method (built vessel tree) against the reference vessels marked in the reference image data sets.

Experiments were performed on two collections consisting in total of 45 3D CTA scans—Collection #1 and Collection #2. Collection #1 contained 30 CTA scans with isotropic voxel in-plane dimensions varying from 0.32 to 0.96 mm and slice spacing ranging from 0.29 to 1.6 mm with a minimum of 457 and maximum of 2451 voxel slices with 512×512 in-plane dimension in each. Each scan corresponded to one of three different body regions: head & neck, abdomen or legs. Each group contained 10 scans.

Collection #2 contained 15 head & neck CTA scans from the training set of the Carotid Lumen Segmentation and Stenosis Grading Challenge [K. Hameeteman, M. A. Zuluaga, M. Freiman, L. Joskowicz, O. Cuisenaire, L. F. Valencia, M. A. GUlsun, K. Krissian, J. Mille, W. C. Wong et al., "Evaluation framework for carotid bifurcation lumen segmentation and stenosis grading," Medical Image Analysis, vol. 15, no. 4, pp. 477-488, 2011.]. The isotropic voxel in-plane dimensions are between 0.23 and 0.59 mm and the slice spacing ranges from 0.44 to 0.6 mm with a minimum of 466 and maximum of 786 slice with 512×512 in-plane dimensions in each. The centerlines of major arteries in Collection #1 were labelled by three observers and then all merged to final reference centerlines. Collection #2 contained carotid lumen segmentations performed by three different experts which were combined to a reference standard for Carotid Bifurcation Lumen Segmentation and Stenosis Grading Challenge [see above].

The segmentation masks were skeletonised to centerlines by the 3D thinning algorithm proposed by Lee et al. [T.-C. Lee, R. L. Kashyap, and C.-N. Chu, "Building skeleton models via 3-d medial surface/axis thinning algorithms," CVGIP: Graph. Models Image Process., vol. 56, no. 6, pp. 462-478, Nov. 1994.]. Finally, the extracted skeleton was corrected by an additional expert and the results are taken as a reference standard for Collection #2.

Human body contains a large number of arteries which then branch out into many smaller arterioles and capillaries. As one can imagine it is almost impossible to have all those vessels be annotated by a medical expert. In order to evaluate objectively the algorithm performance we have evaluated manually how much of the tracked result is not actually representing any kind of a vessel. In general the semi-automated algorithm produced slightly cleaner vessel trees in some scans. Therefore, we would like to summarize the issues encountered in the vessel trees produced by the fully-automated algorithm as there were more problems noted.

Of all scans from the Collection #1 the biggest problems were encountered in the head & neck scans. In three scans tiny bone structures consisting of 3-4 segment nodes were mistakenly connected to the vessel tree. Only in one scan there were two such tiny structures. In two scans tiny strongly calcified objects were detected. In the abdominal scans only one scan had a wrong tiny bone structure. In the leg dataset in three scans tiny calcified objects were mistakenly connected to the tree.

In the Collection #2 only in two scans minor problems were encountered. In both cases tiny bone structures of 1-3 segment nodes were taken as a part of the vessel tree. Overall in 64.44% of scans no non-vessel structures were identified. In 14.44% cases tiny bone objects containing 1-4 points were mistakenly tracked. In 10% cases tiny calcified objects were connected. In 11.1% small non-vessel like structures were detected wrongly.

The body part detection step was evaluated with Collection #1. 10-fold cross-validation (CV) was utilized in order to estimate the h-map values of the deliberately left-out scans. Each test contained three scans, one per body region. The group memberships were found randomly. The parameters were set according to Major et al. (see above). An overall average slice height deviation from the true height of 40.68±77.93 mm was achieved. As a next step the set of slices where the arteries of interest are present were detected. This was achieved by analyzing the regressed slice h-positions. For each $\theta$ the average lower and upper bounds in the h-space were learned in each CV run, and the learned values in the unseen scans were queried. We measured the Jaccard similarity as the overlap measure of detected regions to ground-truth regions.

The slices of AO had an overlap of 78.7%, of AOA yielded 54.1%, of LCI yielded 42.8%, of RCI resulted in 47.2%, of LCC resulted in 73.8% and of RCC delivered 64.8%. Every dataset in Collection #1 had overlap with the ground-truth region except of one showing the legs where LCI-slices were found slightly below the correct region due to the highly pathologic appearance of the vessel tree.

The vessel regression part of the algorithm was evaluated on Collection #1 with the same 10-fold CV setup as described above for evaluation of the body part detection step.

After the slices of $\theta$ were detected, the slice position regression models were trained and applied. The models were trained in the 10-fold CV runs on scans where the artery of interest $\theta$ was present. We measured how many of the regressed positions were falling into the vessel lumen on a slice-basis and on a dataset-basis (see table below).

|         | AO     | AOA       | LCI      | RCI      | LCC    | RCC      |
|---------|--------|-----------|----------|----------|--------|----------|
| 5-best  | 0.92/1 | 0.62/0.7  | 0.78/0.9 | 0.85/0.9 | 1/1    | 0.9/0.9  |
| 10-best | 0.96/1 | 0.64/0.8  | 0.74/0.9 | 0.87/1   | 0.95/1 | 0.89/0.9 |
| 20-best | 0.98/1 | 0.55/0.8  | 0.85/1   | 0.84/1   | 0.95/1 | 0.86/0.9 |

We chose the 20-best positions result as it performed best in overall, vessel lumen candidates were found for all datasets except for 2 datasets at AOA and 1 dataset for RCC. These were due to a very marginal field-of-view of the AOA in one case and two vein outlier cases.

The performance of the semi- and fully automated vessel tracking part of the method on head & neck, abdomen and leg arteries was verified on Collection #1 (see Graph 1 below). A reference point was considered tracked if it was encountered within a sphere of any tracked point with the radius of the sphere being equal to the radius estimated at that tracked point. Distances between reference and corresponding closest tracked points resulted into overall centerline extraction errors.

Left and right common carotid arteries (LCC and RCC) have been fully detected in both semi- and fully-automated cases which is not surprising because in the semi-automated mode the starting positions in both vessels have been provided, and in the fully-automated case the vessel regression step for both vessels reached very high detection accuracy rates. This part of the method coped pretty well with both left and right external carotid arteries (LEC and REC) with both initialization modes. Slightly lower detection rates were reached for the REC due to the fact that it was missed in one dataset and almost missed in the other one due to a very calcified region around the branching point from the RCC to REC. In both initialization modes, high values have also been reached for the Brachiocephalic trunk (BT) (except one dataset where it was completely missed), left internal carotid (LIC) and right subclavian (RS). Slightly lower values for the right internal artery (RIC) were due to a very calcified and plaque region around the branching point. Left subclavian (LS), left and right vertebral arteries (LV and RV) were missed in three (LV) and two (RV) scans respectively due to an insufficient initialization at the aortic arch (AOA). On the other hand, in the fully automated mode, the algorithm performed much better in detecting LS and LV due to a precise detection of points at the AOA by the vessel regression algorithm. The Basilar artery (BA) was missed in two scans in which RV and LV were also missed. The centerline extraction algorithm performed very well and the average errors of 0.95 mm for semi- and 0.93 mm for fully-automated modes were achieved. Despite the above-mentioned problems and limitations the average detection rates were 77% for fully- and 80% for semi-automated modes.

Both modes of the algorithm performed splendidly on the abdominal scans (average 88% for fully- and 96% for semi automated modes) except for the inferior mesenteric artery which was missed in one scan due to its large intensity level difference comparing to the aorta intensity value in the area around the branching point. The average centerline error for both modes was around 2.08 mm. The algorithm successfully detected the main arteries of interest in the leg scans. Those include Aorta (AO), left and right common iliac (LCI and RCI), left and right deep femoral and femoral (LDF, RDF, LF, RF) and left internal iliac arteries (LII). Slightly lower detection rate for the right internal iliac artery was due to its absence in the result of the algorithm on one scan. The low values for the other arteries are due to the artery bypasses present in those scans. All those vessels have been detected by both the seed detection and segment tracking steps but have not been connected to the main tree by the tree growing step. Despite this problem average detection rates were 81% for semi- and 81.6% for fully-automated versions. Average centerline errors were around 1.22 mm for both modes. For some vessels in head & neck and peripheral scans fully automated method outperformed the semi-automated one. It happened due to a more complete initialization in the fully automated case where multiple positions were provided automatically instead of only one per vessel manually chosen in the semi-automated mode.

As a conclusion, the accurate body part detection and body-part specific seed detection and filtering algorithms ensure an excellent initialization for the very accurate segment tracking procedure.

The precise vessel regression approach gives a sharp start for the final body-part specific vessel tree growing method. The performance evaluation on the different datasets demonstrated impressive detection and centerline accuracy rates on scans from all parts of the human body. Besides in the evaluation comparisons against the real medical data it has become clear that the algorithm is capable of estimating anatomically correct radii at intermediate vessel locations. Except of few issues with tiny structure being connected to the main vessel tree, the algorithm demonstrated its robustness and general applicability to the input data.

The invention claimed is:

1. A method for analyzing a slice-based scanned image volume of a body represented by a digital image representation, the method comprising:
   determining a body region to which the slice-based scanned image volume belongs;
   determining expected vessel characteristics for vessels that are located in the determined body region, the expected vessel characteristics including vessel radii, thresholds for a measure of circularity of the respective vessels at a given position, vessel intensity value thresholds, and anatomy-based vessel segment connection rules;
   determining seed points in the image volume representing centers of vessels;
   tracking unconnected vessel segments with the seed points as a starting point by iteratively determining subsequent neighboring seed candidates which are selected based on a value representing a likeliness for a point of a slice-based representation belonging to one of the vessels including the expected vessel characteristics; and
   iteratively extending a vessel tree by connecting the unconnected vessel segments, applying a set of connection rules to the unconnected vessel segments in each iteration of the iteratively extending step based on the expected vessel characteristics, and terminating the iteration when none of a set of connection rules is fulfilled.

2. The method according to claim 1, wherein the step of determining the body region to which the slice-based scanned image volume belongs includes using a slice-based regression method applied to tissue composition in slices of the slice-based scanned image volume.

3. The method according to claim 1, wherein the step of determining the seed points in the image volume representing centers of vessels includes:
   pre-selecting candidate seed points by excluding seed points having an intensity below a predetermined threshold;
   detecting a shape of vessel-shaped objects through edge detection of the vessels through gradient estimation; and
   seed filtering by excluding candidate vessel positions which do not have a sufficiently circular shape in a transversal plane, which is evaluated by determining whether each of the vessel positions has a relative distance parameter below a predetermined threshold.

4. The method according to claim 1, wherein the step of tracking the unconnected vessel segments is initiated by a user selecting one of the determined seed points.

5. The method according to claim 1, further comprising associating a position of slice ranges to the body region by using machine learning techniques.

6. The method according to claim 1, wherein seed points are excluded as the seed candidates based on a comparison of a diameter value associated with the respective seed candidate against expected diameter values for the body region where the seed points are determined in the step of determining the seed points.

7. The method according to claim 1, further comprising optimizing an extension of the vessel tree by connecting the unconnected vessel segments using a genetic algorithm to optimize body-part specific parameters that define the vessel segment connection rules.

8. A non-transitory computer readable medium including a computer program product adapted to carry out the method of claim 1 when run on a computer.

* * * * *